United States Patent
Johansson et al.

(10) Patent No.: US 12,426,656 B2
(45) Date of Patent: Sep. 30, 2025

(54) HEARING PROTECTION DEVICE, COLLISION WARNING SYSTEM AND METHOD OF RETROFITTING A HEARING PROTECTION DEVICE WITH A DETECTION UNIT

(71) Applicant: 3M INNOVATIVE PROPERTIES COMPANY, St. Paul, MN (US)

(72) Inventors: Magnus S. Johansson, Jönköping (SE); Abel Gladstone Mangam, Värnamo (SE); Patrick R. T. Hjort, Värnamo (SE); Henning T. Urban, Kuehlungsborn (DE)

(73) Assignee: 3M Innovative Properties Company, St. Paul, MN (US)

( * ) Notice: Subject to any disclaimer, the term of this patent is extended or adjusted under 35 U.S.C. 154(b) by 37 days.

(21) Appl. No.: 18/258,218

(22) PCT Filed: Dec. 9, 2021

(86) PCT No.: PCT/IB2021/061509
§ 371 (c)(1),
(2) Date: Jun. 19, 2023

(87) PCT Pub. No.: WO2022/137000
PCT Pub. Date: Jun. 30, 2022

(65) Prior Publication Data
US 2024/0041147 A1 Feb. 8, 2024

(30) Foreign Application Priority Data
Dec. 23, 2020 (EP) .................................... 20217109

(51) Int. Cl.
*A42B 1/0188* (2021.01)
*A42B 3/16* (2006.01)
(Continued)

(52) U.S. Cl.
CPC ............ *A42B 1/0188* (2021.01); *A42B 3/166* (2013.01); *G01S 11/06* (2013.01); *G01S 11/08* (2013.01)

(58) Field of Classification Search
CPC ....... A42B 1/0188; A42B 3/166; G01S 11/06; G01S 11/08
See application file for complete search history.

(56) References Cited

U.S. PATENT DOCUMENTS 7,319,399 B2   1/2008   Berg
9,955,264 B2   4/2018   Brayton
(Continued)

FOREIGN PATENT DOCUMENTS

CA   3128082 A1 *   8/2020   ........... G01S 13/931
CN   109752686 B  *   12/2011
(Continued)

OTHER PUBLICATIONS

Extended European Search Report received for EP Patent Application No. 20217109.6, mailed on Jun. 11, 2021, 3 pages.
(Continued)

*Primary Examiner* — Chico A Foxx
(74) *Attorney, Agent, or Firm* — Katherine M. Scholz; Jonathan V. Sry

(57) ABSTRACT

Hearing protection device (10, 10', 10") with an indication unit (40a, 40b) and a detection unit (30, 30', 30") to send a first detection signal, to assign a distance value based on a second detection signal of an external device (50, 50) representing the physical distance to the external device (50, 50) and to control the indication unit (40a, 40b) to provide an indication to the user (100) if the assigned distance value is at or below a predetermined threshold distance value. Thus, a collision may easily and reliably be prevented by providing an indication to the user (100), so that the risk of
(Continued)

missing relevant sound of a moving person or object is overcome. A collision warning system comprising such a hearing protection device (10, 10', 10") and an external device is also provided. Furthermore, a method of retrofitting a hearing protection device (10''') with such a detection unit (30, 30', 30") is provided.

18 Claims, 11 Drawing Sheets

(51) Int. Cl.
  *G01S 11/06* (2006.01)
  *G01S 11/08* (2006.01)

(56) References Cited

U.S. PATENT DOCUMENTS

| | | | |
|---|---|---|---|
| 10,109,164 B2 | 10/2018 | Brayton et al. | |
| 10,129,633 B1 * | 11/2018 | Patil | G08B 13/19663 |
| 10,896,667 B2 * | 1/2021 | Muggleton | G06F 16/29 |
| 2014/0266789 A1 * | 9/2014 | Matus | H04Q 9/00 340/870.07 |
| 2015/0055784 A1 | 2/2015 | Brayton et al. | |
| 2017/0188129 A1 * | 6/2017 | Sindia | H03G 3/3005 |
| 2017/0374455 A1 | 12/2017 | Shastry et al. | |
| 2018/0235117 A1 * | 8/2018 | Feri | H05B 47/105 |
| 2019/0057584 A1 | 2/2019 | Brayton et al. | |
| 2019/0083320 A1 | 3/2019 | Gustavsson et al. | |
| 2022/0264219 A1 * | 8/2022 | Keikhosravy | H04R 3/005 |

FOREIGN PATENT DOCUMENTS

| | | | | |
|---|---|---|---|---|
| CN | 104118395 A | * | 10/2014 | G06K 7/10069 |
| CN | 105632145 A | | 6/2016 | |
| CN | 106114681 A | * | 11/2016 | B62D 65/005 |
| CN | 207468161 U | * | 6/2018 | |
| CN | 104118395 B | * | 8/2018 | G06K 7/10069 |
| CN | 110232320 B | | 7/2021 | |
| EP | 1629801 B1 | | 6/2009 | |
| EP | 2811476 A2 | | 12/2014 | |
| KR | 20110065081 A | * | 6/2011 | |
| WO | 2006058319 A1 | | 6/2006 | |
| WO | 2009131518 A1 | | 10/2009 | |
| WO | WO-2012007475 A1 | * | 1/2012 | A42B 3/14 |
| WO | 2017011911 A1 | | 1/2017 | |
| WO | WO-2017118571 A1 | * | 7/2017 | A42B 3/16 |
| WO | 2017196231 A1 | | 11/2017 | |
| WO | 2018018574 A1 | | 2/2018 | |
| WO | 2018148356 A1 | | 8/2018 | |
| WO | WO-2019104172 A1 | * | 5/2019 | A61B 5/0006 |

OTHER PUBLICATIONS

International Search report for PCT International Application No. PCT/IB2021/061509, mailed on Feb. 23, 2022, 6 pages.

* cited by examiner

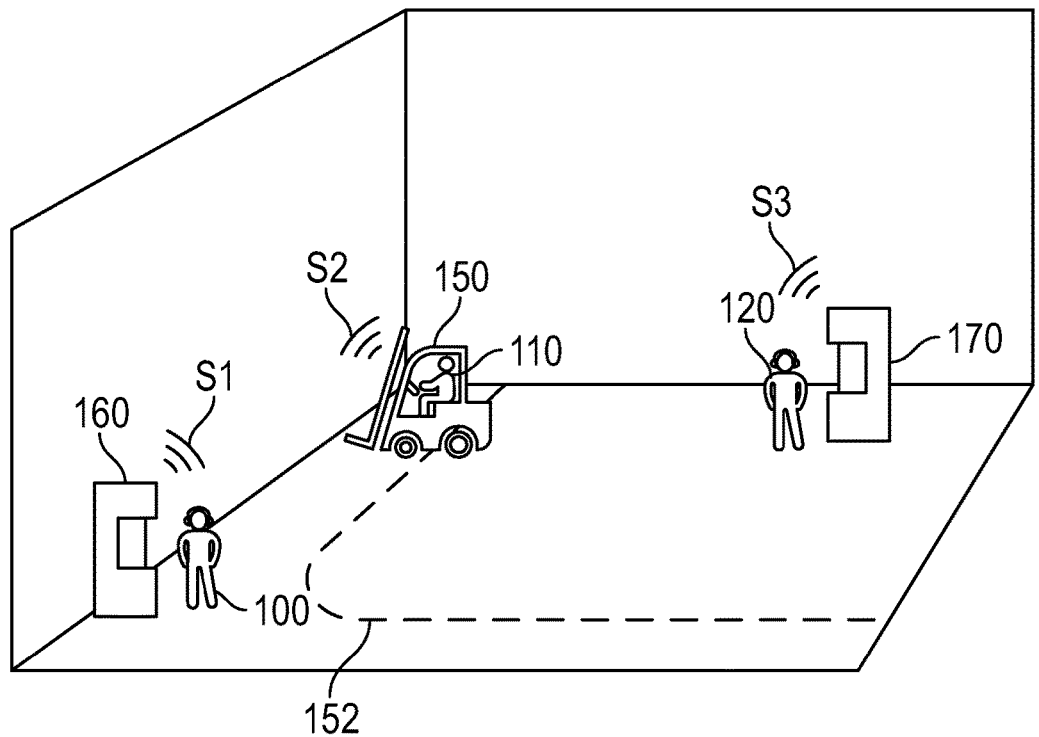
FIG. 3
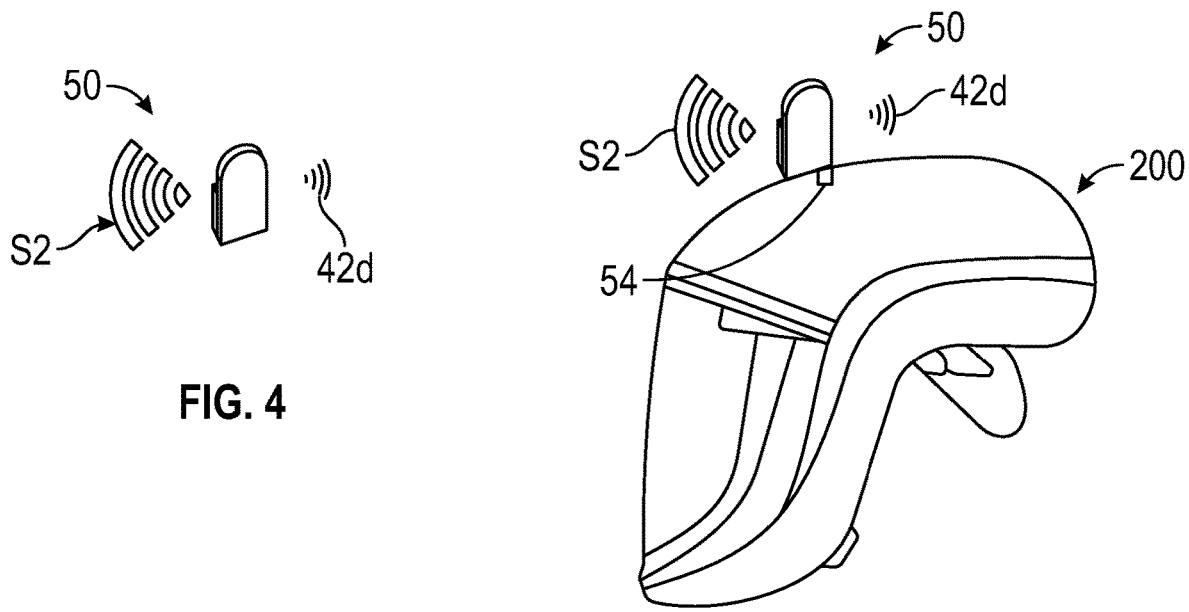
FIG. 4
FIG. 5

HEARING PROTECTION DEVICE, COLLISION WARNING SYSTEM AND METHOD OF RETROFITTING A HEARING PROTECTION DEVICE WITH A DETECTION UNIT

CROSS REFERENCE TO RELATED APPLICATIONS

This application is a national stage filing under 35 U.S.C. 371 of PCT/IB2021/061509, filed Dec. 9, 2021, which claims the benefit of EP application Ser. No. 20/217,109.6, filed Dec. 23, 2020, the disclosure of which is incorporated by reference in its/their entirety herein.

The present disclosure relates to a hearing protection device with an indication unit and a detection unit. Furthermore, the present disclosure relates to a collision warning system and to a method retrofitting a hearing protection device with a detection unit.

Hearing protection devices are typically used in noisy environments for protecting a wearer's hearing from noise at potentially harmful noise levels. Typically, hearing protection devices have two muffs or caps which cover the ears of the wearer and which are connected to one another by a headband. Each cup typically is further formed by a rigid shell that is furnished with a noise dampening material, for example a foamed material.

There is a general desire to make hearing protection devices sufficient for persons that are in noisy environments for longer times. While noise dampening is the essential purpose of a hearing protection device, there is often a need for the wearer to hear certain sounds from the environment, like acoustic signals from other persons or objects in order to be aware of persons or objects moving towards the wearer of a hearing protection device, in order to be aware of persons or objects approaching towards the wearer. These acoustic signals may include, for example, voice signals, alarm sounds such as a signal horn or wheel and driving noise of a vehicle.

Although there are active hearing protection devices on the market which have passive noise dampening properties and additionally are configured to transmit sounds from the environment into the ear cup via active electronics connected to a microphone outside the ear cup and a loudspeaker inside the ear cup, there might be the risk that such acoustic signals are not transmitted into the ear cup. This may lead to dangerous situations for the wearer.

An attempt to address this drawback is that the active hearing protection device may be configured to let such sound relevant for the wearer pass through or even transmit this into the earcup. WO 2006/058319 for example discloses a hearing protection device including a sound attenuating body and an electronic unit having a microphone, an amplifier, and a loudspeaker, where the electronic unit is selectively activated and, when activated, receives sound from an ambient environment, amplifies a frequency range of the received sound corresponding to a frequency range of human speech, and varies said amplification such that a total level of sound passing through the body and through the electronic unit does not exceed a maximum predetermined sound level. Such solutions may, on the one hand, make a hearing protection device more complex and expensive, and, on the other hand, there may still be the risk that such relevant sounds are not apparent to the wearer.

Although existing active hearing protection devices have a variety of advantages there is still a need for a hearing protection device overcoming the aforementioned drawbacks. It is therefore an object of the present disclosure to provide a hearing protection device addressing the risk of not hearing warning sounds when wearing a hearing protection device as well as addressing a collision risk caused by other persons or objects moving towards the wearer of the hearing protection device.

In a first aspect, the present disclosure relates to a hearing protection device comprising two earmuffs or ear plugs, an indication unit for providing an indication to a user of the hearing protection device and a detection unit. The detection unit comprises a transmitter for sending out a first detection signal and a receiver for receiving a second detection signal from an external device. The detection unit is configured to assign a distance value representing the physical distance to the external device based on the second detection signal. The detection unit is configured to control the indication unit such that the indication unit provides the indication to the user if the assigned distance value is at or below a predetermined threshold distance value. In other words, the detection unit is enabled to determine the distance to the external device by receiving the second detection signal from the external device and to compare the determined distance with a stored distance value under which a distance to the external device is considered critical. The advantage of such a hearing protection device is that a reliable prevention of a collision of the wearer with other persons or objects is minimized or avoided in an easy and reliable way. Also, the risk of overhearing relevant sounds is thereby compensated. The indication to the user may comprise an optical, audible and/or haptic indication or feedback to the user.

In a second aspect, the present disclosure relates to a collision warning system comprising a hearing protection device according to the present disclosure and at least one external device. The external device comprises a detection unit comprising a transmitter for sending out a second detection signal and a receiver for receiving a first detection signal sent by the hearing protection device. The detection unit is configured to assign a distance value representing the physical distance between the hearing protection device and the at least one external device based on the received first detection signal. The external device optionally comprises an indication unit for providing an indication to a user of the hearing protection device and wherein the detection unit is configured to control the indication unit such that the indication unit provides the indication to the user of the hearing protection device if the assigned distance value is at or below a predetermined threshold value. In other words, the detection unit is enabled to determine the distance between the hearing protection device and the external device by receiving the received first detection signal from the hearing protection device (and based on the received second detection signal from the external device) and to compare the determined distance with a stored distance value under which a distance between the hearing protection device and the external device is considered critical. The advantage of such a hearing protection device is that a reliable prevention of a collision of the wearer with other persons or objects is minimized or avoided in an easy and reliable way. Also, the risk of overhearing relevant sounds is thereby compensated. The indication may comprise an optical, audible and/or haptic indication or feedback to the user.

In a third aspect, the present disclosure relates to a method of retrofitting a hearing protection device with a detection unit. The method comprises the steps of: providing a hearing protection device comprising two earmuffs or ear plugs, providing a detection unit comprising a transmitter for sending out a first detection signal, a receiver for receiving a second detection signal sent by an external device. The detection unit is configured to assign a distance value representing the physical distance to the external device based on the received second detection signal. The detection unit is configured to provide an indication to the user of the hearing protection device if the assigned distance value is at or below a predetermined threshold value. The method further comprises the step of attaching the detection unit to the hearing protection device. The advantage of such method of retrofitting a hearing protection device is that a reliable prevention of a collision of the wearer with other persons or objects is minimized or avoided in an easy and reliable way even with a hearing protection device which originally did not have that functionality. Also, the risk of overhearing relevant sounds is thereby compensated. The indication may comprise an optical, audible and/or haptic indication or feedback to the user.

Personal protective equipment within the meaning of the present disclosure includes protective helmets, welding shields, protective face shields, protective clothing such as jackets, gloves or the like. Typically, the personal protective equipment comprises specific protection means to protect the user or wearer of it from impact or injuries acting on the user or wearer. For example, the hazards addressed by personal protective equipment comprise physical, electrical, heat, chemical, biohazards and airborne particulate matter. For some working conditions, personal protective equipment may be required by the employer or by law or comparable regulations.

Active or passive noise reduction or cancellation within the meaning of the present disclosure is understood as measures in a headset that reduce unwanted ambient sound. This may be achieved by passive measures, e. g. where the cups and cushions of the headset comprise damping material and wherein the cushions cover the user's ears. Alternatively or in addition to passive noise reduction or cancellation, active noise reduction or cancellation uses a technology where the ambient sound is captured by a microphone and inverted sounds waves, i. e. sound waves being exactly out of phase, are being generated and played via loudspeakers in the headset to the user in parallel to the ambient noise reaching the user's ears. Typically, these opposite sounds waves collide and eliminate each other or cancel each other.

A hearing protection device (HPD) within the meaning of the present disclosure is a personal protective equipment that comprises an ear protection worn in or over the ears while being exposed to hazardous or irritating ambient sounds or noise. An HPD helps to prevent noise-induced hearing impairment or even loss. HPD's may comprise earmuffs or earplugs. To achieve the protection, HPD's typically comprise active and/or passive noise reduction of cancellation means as described above. HPD's may typically also comprise a headband for connecting the two earmuffs or ear plugs and to keep these in position when the HPD is worn by a worker or user.

An external device within the meaning of the present disclosure is understood as a separate, preferably self-contained device being spaced apart from a hearing protection device. Such an external device may be attachable to a vehicle, a person and/or personal protective equipment worn by a user. An external device may comprise certain electronic components for functionality desired or needed by a user of such an external device including a detection and/or indication unit. It is also conceivable that the indication unit is spaced from the external device in a separate housing.

An indication within the meaning of the present disclosure is understood as giving a signal or feedback to the user or wearer of a device about a relevant activity or status or condition. Such an indication may comprise an acoustic indication, e. g. a sound played to the user, an optical indication, e. g. a light signal beamed so that a user can see it, or a haptic indication, e. g. a motor producing a vibration which can be sensed by the user. It is conceivable to arrange more than one way of indication in parallel, depending on the conditions under which the user is. For example, if an acoustic indication may be overheard due to a high noise level surrounding the user, it may be useful to have another indication given in parallel, e. g. an optical or a haptic indication. Other combinations of indications are conceivable as well.

Physical distance within the meaning of the present disclosure is the shortest distance in [m] between two objects measured in a straight line.

Distance value within the meaning of the present disclosure is a value in [m] which is assigned based on a received electronic signal.

A predetermined threshold distance value within the meaning of the present disclosure is understood as a value in [m] representing a critical distance between two objects, e. g. two users, a user and a vehicle or two vehicles, under which—without measure of control or counter steering—a collision may occur leading to impact or injuries to the user and/or the vehicle. Predetermined is understood as a preparational set up of the value based on a specific situation or need of a user. For example, if the user is walking, the value may be larger compared to a user driving with a vehicle. For example, this set up may be done manually by a user or automatically by a system taking into account the circumstances of the user and his surrounding including moving objects like persons, vehicles etc.

Detection signal within the meaning of the present disclosure is an electronic signal sent out by an HPD to an external device. A detection signal may also be sent out by an external device and be received by the HPD. Such a detection signal may have different characteristics such as signal strength, time of flight etc. These characteristics of the detection signal may depend on the distance over which the signal is being sent. For example, the signal strength is a characteristic which changes over the distance along which the signal is being sent, i. e. the longer the distance, the lower the signal strength at the point of receipt. According to the law of physics, i. e. the distance law, the signal strength, as other radiation, too, lowers depending on the square of the radius r from the signal source to the signal receiving location. In other words, the intensity at the receiving location follows the equation $I_R \propto$ (i. e. is proportional) $1/r^2$. Another example of a distance-depending characteristic is the time of flight. Typically, the time of flight is the time delay between the start time of sending out a signal to the time of receiving a corresponding signal back from the device located at a certain location spaced from the point of sending. The longer the distance, the longer the time of flight of the signal. Typically, there is a proportional relationship between the distance and the time of flight as the signal usually travels with a constant speed of approx. 300000 km/s (in a vacuum or in air).

Ultra-wideband (UWB) is a radio technology for short-range, high bandwidth communications between electronic devices. UWB typically uses very low energy. The typical applications are data collection, precision locating and tracking applications.

Bluetooth signal is a wireless technology standard for data exchange between electronic devices over short distances. A specific standard within the Bluetooth standard is Bluetooth Low Energy (BLE or BTLE), which particularly aims at low energy consumption for this exchange.

Identification (ID) or identification information within the meaning of the present disclosure is understood as signal information for identifying (a device of) a person or an object sending a signal. Typically, a code comprising an information uniquely associable to a person or object is added to a signal. An object or person identification may be achieved thereby in an easy and reliable way.

Attachment means within the meaning of the present disclosure comprise means for permanently or temporarily attaching a device or component to another device. For example, a self-contained unit like a detection unit or indication unit may be attached to a headset or a hearing protection device, respectively. Furthermore, such a self-contained unit may be attached to a vehicle or part thereof, or to personal protective equipment. Suitable attachment means comprise mechanical attachment means such as clips, clamps, hook and loop fasteners, screws, bolts, rivets or the like. Also, adhesive attachment means are conceivable such as adhesive tapes or patches, spray adhesive or liquid adhesive applied to the location of attachment. It is also conceivable to combine mechanical and adhesive attachment means, if a specific attachment requiring this is necessary. The selection of the attachment means may depend on whether or not a permanent attachment is required or whether the unit may need to be detached from the other part or device.

In one embodiment, the detection unit of the hearing protection device is configured to assign the distance value based on a characteristic of the received second detection signal. The advantage of such a detection unit is that an easy and reliable assignment of a distance value is achieved with such a detection unit. Using a characteristic of the received detection signal enables the detection unit to carry out an accurate distance assignment.

In another embodiment, the first and second detection signals are ultra-wide band (UWB) signals, wherein the characteristic of the received second detection signal is the time of flight. The advantage of such an UWB signal is that it provides for an easy and reliable detection signal allowing an accurate assignment of a distance value.

In a further embodiment, the first and second detection signals are Bluetooth signals, wherein the characteristic of the received second detection signal is the received signal strength. Preferably, the first and second detection signals are Bluetooth Low Energy signals. The advantage of such a Bluetooth signal is that it provides for an easy and reliable detection signal allowing an accurate assignment of a distance value. The particular advantage of a Bluetooth Low Energy signal is that the detection occurs with a low energy consumption, which helps to save energy of the power supply of a hearing protection device which comprises such a detection unit sending a Bluetooth Low Energy signal.

In a certain embodiment, where the first and second detection signals are Bluetooth signals and where the characteristic of the received second detection is the received signal strength, the characteristic further includes the direction in which the external device is located relative to the hearing protection device. The advantage of including the direction is that a higher accuracy is achieved for the detection and the assignment of the distance value, respectively.

In yet another embodiment, the first and/or the second detection signal comprises an ID assigned to the hearing protection device and/or the user thereof. The advantage of including an ID in the detection signal is that an object or person identification may be achieved thereby in an easy and reliable way. Such identification may further enhance the system accuracy, i. e. the system is aware of which persons or object may move towards each other.

In a further embodiment, the predetermined threshold distance value is being set up by the user. The advantage of the user set up the threshold distance value is that it can be individually set up according to the user's needs. It is to be noted that the predetermined threshold distance value may be different for different HPD's and/or external devices taking the individual circumstances into account, e. g. which object, moving speed etc. It is conceivable to use further sensors to detect movement etc. of the object itself or the user and to feed that information to the detection unit to enhance the detection accuracy and the set-up of the values.

In yet a further embodiment, the predetermined threshold distance value is being set up by the detection unit, preferably depending on the received ID information, i. e. a person, a vehicle etc. The advantage of the set-up of the threshold distance value by the detection unit is that an automatic set-up may be achieved thereby avoiding the risk of a wrong set-up by a user. As mentioned above for the individual set-up of the predetermined threshold distance value by the user, it may also be the case that for an automatic set-up of that value, the value is different for an HPD and an external device, respectively, based on the individual circumstances of the user or devices, e. g. moving speed etc. Similarly, it may also be conceivable to use further sensors to detect movement etc. of the object itself or of the user and to feed that information into the detection unit to enhance the detection accuracy and the set-up of the values.

In one embodiment, the hearing protection device comprises two earmuffs each having a cup and a cushion, the hearing protection device further comprising active and/or passive noise cancellation means. The advantage of a hearing protection device with noise cancellation is that an easy and reliable protection of the user's or worker's ears is achieved thereby avoiding hearing loss or impairment.

In a certain embodiment, the hearing protection device comprises a headband for connecting the two earmuffs. The advantage of such a headband is that an easy and reliable way of connecting the earmuff is provided thereby.

In one embodiment, the hearing protection device comprises attachment means for attaching the two earmuffs to a protective helmet. The advantage of such attachment means is that the earmuff may be easily and reliably attached to a helmet and that wearing a helmet does not interfere with the hearing protection device and its earmuffs.

In another embodiment, the hearing protection device comprises a loudspeaker for playing an audio signal to the user of the hearing protection device, wherein the detection unit is configured to control the loudspeaker of the hearing protection device such that the loudspeaker provides an indication to the user of the hearing protection device if the assigned distance value is at or below the threshold value. Such a loudspeaker may provide for an easy and reliable indication to the user. Also, the loudspeaker may be used for other functions in a hearing protection device, e. g. voice communication, or may be part of a noise cancellation system or radio etc. Furthermore, some hearing protection devices already comprise loudspeakers which could be easily used for the acoustic indication.

In a further embodiment, the detection unit and the indication unit of the hearing protection device are contained in a mounting ring attached to the earmuffs between the cup and the cushion. The advantage of such an arrangement is that an easy, quick and reliable mounting of the detection unit and the indication unit may be achieved thereby which may help to simplify a retrofit of a hearing protection device or the general assembly of it. Also, a compact design may be achieved thereby.

In one embodiment, the indication unit of the hearing protection device is contained in a separate housing and is spaced from the hearing protection device. The indication unit optionally comprises attachment means for attachment to the user or personal protective equipment worn by the user of the hearing protection device. The arrangement of the indication unit in a separate housing allows for a greater freedom of design and usage because two smaller units may be better and easier placed when using personal protective equipment.

In another embodiment, the indication to the user provided by the indication unit of the hearing protection device comprises an optical, an audible and/or a haptic indication. The advantage of such an indication to the user is that these indications provide easy and reliable indication or feedback to the user about the detection. It is conceivable to combine one indication with one or more at a time, in order to prevent that such an indication might be overlooked, e. g. in a light environment, or overheard, e. g. in a noisy environment. Providing an additional indication helps to reduce the risk of the user to be unaware of the indication in certain circumstances.

In a further embodiment, the first and/or second detection signal is sent along constant intervals interrupted by constant intervals of no signal sent. The advantage of such constant intervals is that an easy and reliable set-up of the detection unit is achieved thereby.

In yet a further embodiment, the first and/or second detection signal is sent along variable intervals interrupted by variable intervals of no signal sent. The advantage of such variable intervals is that a higher accuracy, in particular for the detection under changing circumstances like movement etc., may be achieved thereby, i. e. enhancing the accuracy for moving users or objects.

In one embodiment of the collision warning system, the detection unit of the external device is configured to assign the distance value based on a characteristic of the received first detection signal. The advantage of such a detection unit is that an easy and reliable assignment of a distance value is achieved with such a detection unit. Using a characteristic of the received detection signal enables the detection unit to carry out an accurate distance assignment.

In another embodiment of the collision warning system, the first and second detection signals are ultra-wide band (UWB) signals wherein the characteristic of the received first detection signal is the time of flight. The advantage of such an UWB signal is that it provides for an easy and reliable detection signal allowing an accurate assignment of a distance value.

In a further embodiment of the collision warning system, the first and second detection signals are Bluetooth signals wherein the characteristic of the received first detection signal is the received signal strength. Preferably, the first and second detection signals are Bluetooth Low Energy signals. The advantage of such a Bluetooth signal is that it provides for an easy and reliable detection signal allowing an accurate assignment of a distance value. The particular advantage of a Bluetooth Low Energy signal is that the detection occurs with a low energy consumption, which helps to save energy of the power supply of a hearing protection device which comprises such a detection unit sending a Bluetooth Low Energy signal.

In yet another certain embodiment of the collision warning system, the characteristic further includes the direction in which the external device is located relative to the hearing protection device. The advantage of including the direction is that a higher accuracy is achieved for the detection and the assignment of the distance value, respectively.

In yet a further embodiment of the collision warning system, the external device is a hearing protection device, optionally comprising two earmuffs each having a cup and a cushion and active and/or passive noise cancellation means. The advantage of a hearing protection device with noise cancellation is that an easy and reliable protection of the user's or worker's ears is achieved thereby avoiding hearing loss or impairment.

In one embodiment of the collision warning system, the hearing protection device comprises a headband for connecting the two earmuffs. The advantage of such a headband is that an easy and reliable way of connecting the earmuff is provided thereby.

In another embodiment of the collision warning system, the hearing protection device comprises attachment means for attaching the two earmuffs to a protective helmet. The advantage of such attachment means is that the earmuff may be easily and reliably attached to a helmet and that wearing a helmet does not interfere with the hearing protection device and its earmuffs.

In a further embodiment of the collision warning system, the first and/or second detection signal comprises an ID assigned to the hearing protection device and/or the user thereof. The advantage of including an ID in the detection signal is that an object or person identification may be achieved thereby in an easy and reliable way. Such identification may further enhance the system accuracy, i. e. the system is aware of which persons or object may move towards each other.

In yet a further embodiment of the collision warning system, the predetermined threshold distance value of the external device is being set up by the user. The advantage of the set-up of the threshold distance value by the user is that it can be individually set up according to the user's needs. It is to be noted that the predetermined threshold distance value may be different for different HPD's and/or external devices taking the individual circumstances into account, e. g. which object, moving speed etc. It is conceivable to use further sensors to detect movement etc. of the object itself or the user and to feed that information to the detection unit to enhance the detection accuracy and the set-up of the values.

In another embodiment of the hearing protection device, the predetermined threshold distance value of the external device is being set up by the detection unit, preferably depending on the received ID information, i. e. a person, a vehicle etc. The advantage of the set-up of the threshold distance value by the detection unit is that an automatic set up may be achieved thereby avoiding the risk of a wrong set-up by a user. As mentioned above for the individual set-up of the predetermined threshold distance value by the user, it may also be the case that for an automatic set-up of that value, the value is different for an HPD and an external device, respectively, based on the individual circumstances of the user or devices, e. g. moving speed etc. Similarly, it may also be conceivable to use further sensors to detect movement etc. of the object itself or of the user and to feed that information into the detection unit to enhance the detection accuracy and the set-up of the values.

In one embodiment of the collision warning system, the external device is a self-contained device attachable to a person, a vehicle and/or a personal protective device. The advantage of such an external device is that an easy, robust and reliable system is achieved thereby for the collision warning system.

In a further embodiment of the collision warning system, the external device further comprises an indication unit for providing an indication to a user of the external device. Such an indication may comprise an acoustic indication, e. g. a sound played to the user, an optical indication, e. g. a light signal beamed so that a user can see it, or a haptic indication, e. g. a motor producing a vibration which can be sensed by the user. It is conceivable to arrange more than one way of indication in parallel, depending on the conditions under which the user is. For example, if an acoustic indication may be overheard due to a high noise level surrounding the user, it may be useful to have another indication given in parallel, e. g. an optical or a haptic indication. The advantage of such an indication unit is that a reliable indication is provided to the user of the collision warning system. Other combinations are conceivable as well.

In yet a further embodiment of the collision warning system, the indication unit is contained in a separate housing and spaced from the external device, the indication unit optionally comprising attachment means for attachment to the user or personal protective equipment worn by the user of the external device. The advantage of such an indication unit of the external device is that an easy and reliable attachment of the indication unit is achieved used within the collision warning system.

In another embodiment of the collision warning system, the first and/or second detection signal is sent along constant intervals interrupted by constant intervals of no signal sent. The advantage of such constant intervals is that an easy and reliable set-up of the detection unit is achieved thereby.

In yet another embodiment of the collision warning system, the first and/or second detection signal is sent along variable intervals interrupted by variable intervals of no signal sent. The advantage of such an UWB signal is that it provides for an easy and reliable detection signal allowing an accurate assignment of a distance value.

In one embodiment of the collision warning system, the external device comprises a loudspeaker for playing an audio signal to the user of the external device, wherein the detection unit of the external device is configured to control the loudspeaker such that the loudspeaker provides an indication to the user of the external device if the assigned distance value is at or below the threshold value. Such a loudspeaker may provide for an easy and reliable indication to the user. Also, the loudspeaker may be used for other functions in a hearing protection device, e. g. voice communication, or may be part of a noise cancellation system. Furthermore, some hearing protection devices already comprise loudspeakers which would form the indication unit, and which could be easily used for the acoustic indication.

In one embodiment, the detection unit in the method of retrofitting is configured to assign the distance value based on a characteristic of the received second detection signal. The advantage of such a detection unit is that an easy and reliable assignment of a distance value is achieved with such a detection unit. Using a characteristic of the received detection signal enables the detection unit to carry out an accurate distance assignment.

In another embodiment, the method of retrofitting further comprises the step of providing an indication unit for providing an indication to a user of the hearing protection device, wherein the detection unit is configured to control the indication unit such that the indication unit provides the indication to the user of the hearing protection device if the assigned distance value is at or below the threshold value. It is conceivable to combine one indication with one or more at a time, in order to prevent that such an indication might be overlooked, e. g. in a light environment, or overheard, e. g. in a noisy environment. Providing an additional indication helps to reduce the risk of the user to be unaware of the indication in certain circumstances.

In a further embodiment, the hearing protection device in the method of retrofitting comprises a loudspeaker for playing an audio signal to the user of the hearing protection device, wherein the detection unit is configured to control the loudspeaker of the hearing protection device such that the loudspeaker provides an indication to the user of the hearing protection device if the assigned distance value is at or below the threshold value.

Such a loudspeaker may provide for an easy and reliable indication to the user. Also, the loudspeaker may be used for other functions in a hearing protection device, e. g. voice communication, or may be part of a noise cancellation system or radio etc. Furthermore, some hearing protection device already comprise loudspeakers which could be easily used for the acoustic indication.

In a further embodiment, the detection unit in the method of retrofitting is contained in a mounting ring attached to the earmuffs between the cup and the cushion. The advantage of such an arrangement is that an easy, quick and reliable mounting of the detection unit and the indication unit may be achieved thereby which may help to simplify a retrofit of a hearing protection device or the general assembly of it. Also, a compact design may be achieved thereby.

In a yet further certain embodiment, the mounting ring of the method of retrofitting further comprises the indication unit. The advantage of such a mounting ring is that a compact design is even further supported by the arrangement of not only the detection unit, but also the indication unit into the mounting ring.

A hearing protection device according to the present disclosure may be made by arranging a detection unit with its component and units as well as an indication unit with its components and units onto printed circuit boards (PCBs) and to arrange these PCBs at the hearing protection device. In case of earmuffs, the PCBs may be located inside of the hollow shape of one or both earmuffs. Another way to make such a hearing protection device is described above under the method of retrofitting a hearing protection device, where a typical hearing protection device is taken and being retrofitted with such a detection unit and such an indication unit, preferably contained in a mounting ring.

The invention was described in various embodiments above. It is understood by a person skilled in the art, that one, several of or all the above-mentioned embodiments can be combined with each other.

The invention will now be described in more detail with reference to the following Figures exemplifying particular embodiments of the invention:

FIG. 3 is a perspective view of users wearing a hearing protection device as shown in FIG. 1 and of a user with an external device according to an embodiment of the present disclosure;

FIG. 4 is a schematic side view of an external device according to the present disclosure illustrating the second detection signal and an acoustic signal;

FIG. 5 is a schematic side view of the external device as shown in FIG. 4 being attached to personal protective equipment;

Figure 1:
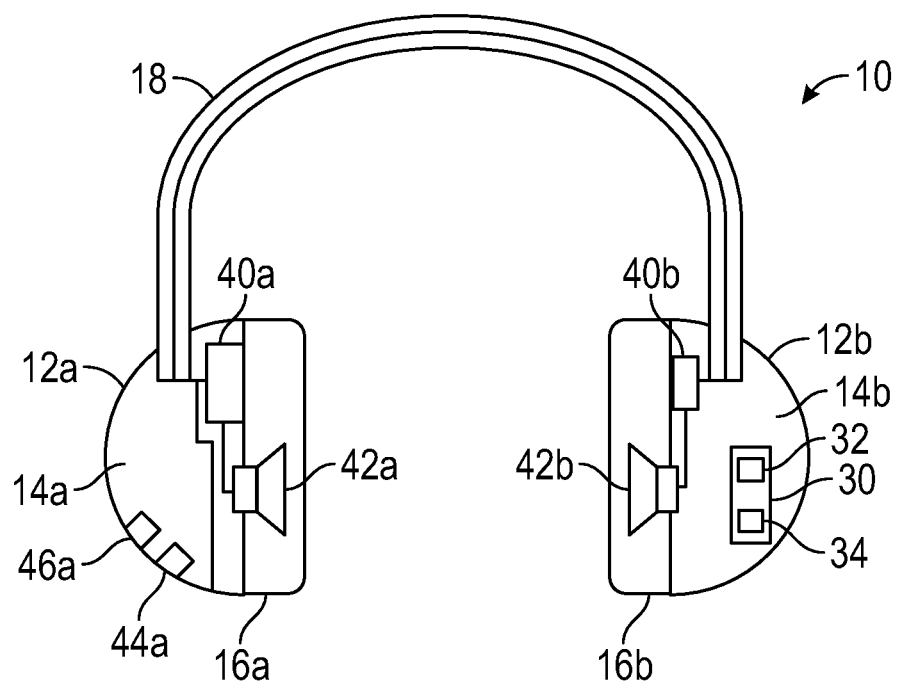
FIG. 1 is a schematic front view of a hearing protection device according to an embodiment of the present disclosure.

FIG. 1 shows in a schematic front view the hearing protection device 10 according to an embodiment of the present disclosure comprising two earmuffs 12a, 12b connected by a headband 18. Each of the earmuffs 12a, 12b comprises an indication unit 40a, 40b each comprising a loudspeaker 42a, 42b for proving an acoustic indication to a user 100 (not shown in FIG. 1), e. g. an audio signal. The hearing protection device 10 further comprises at one of the earmuffs 12b a detection unit 30 comprising a transmitter 32 for sending out a first detection signal and a receiver 34 for receiving a second detection signal from an external device (not shown here). The detection unit 30 is connected to the indication units 40a, 40b, wherein the detection unit 30 is configured to control the indication units 40a, such that the indication units 40a, 40b provide an indication to the user if the assigned distance value is at or below a predetermined threshold distance value. Each of the earmuffs 12a, 12b further comprise a cup 14a, 14b, which is in the embodiment shown in a hollow hemisphere shape. Components of the hearing protection device 10, for example the indication units 40a, 40b, the detection unit 30 and the loudspeakers 42a, 42b are housed within one or both cups 14a, 14b. The earmuffs 12a, 12b further each comprise a cushion 16a, 16b for sealing the earmuffs 12a, 12b of the hearing protection device 10 to the ears of a user (not shown here). In the embodiment shown in FIG. 1, the cushions 16a, 16b are preferably oval shaped. FIG. 1 further shows in one cup 16a an light emitting diode (LED) 44a for providing an optical indication to a user and a vibration motor 46a for providing a haptic indication to a user.

Figure 2:
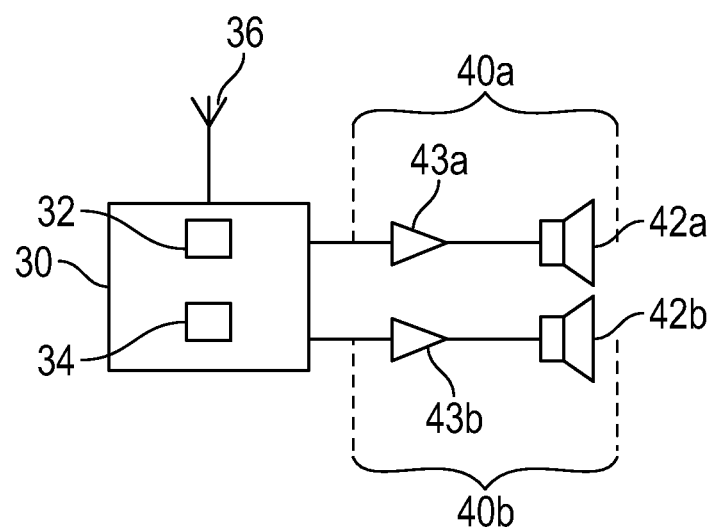
FIG. 2 is a schematic top view of the detection unit and the indication unit of the hearing protection device as shown in FIG. 1.

FIG. 2 shows in a schematic top view the detection unit 30 and the indication units 40a, of the hearing protection device 10. Similar to the embodiment as shown in FIG. 1, the detection unit 30 comprises a transmitter 32 for sending out a first detection signal and a receiver 34 for receiving a second detection signal from an external device (not shown here). The detection unit 30 is connected to the indication units 40a, 40b, wherein the detection unit 30 is configured to control the indication units 40a, 40b such that the indication units 40a, 40b provide an indication to the user if the assigned distance value is at or below a predetermined threshold distance value. In addition to the components of the indication units 40a, 40b as shown in FIG. 1, the indication units 40a, 40b further comprise amplifiers 43a, 43b connected to the detection unit 30 as well as to the loudspeaker 42a, 42b. The amplifiers 43a, 43b may help to enhance the audible indication provided to the user, e. g. to increase the volume and/or to increase the quality of the acoustic signal provided by the loudspeakers 42a, 42b.

FIG. 3 shows in a perspective view the three users 100, 110, 120, two of which are wearing a hearing protection device 10, 10' according to an embodiment of the present disclosure. A first user 100 is wearing a hearing protection device 10 sending out a first detection signal as illustrated by S1. The user 100 is working at a machine 160. A second user 110 is driving a vehicle 150, e. g. a forklift 150, which is equipped with an external device 50 (omitted here for simplification, please see FIG. 8 for more details) sending out a second detection signal as illustrated by S2. The second user 110 drives with the forklift 150 along the driveway as illustrated by 152 thereby approaching the first user 100 with the hearing protection device 10. The second detection signal S2 is received by the receiver 34 of the detection unit 30 of the hearing protection device 10 worn by the first user 100. The detection unit 30 of the first user assigns a distance value representing the physical distance to the external device 50 attached to the forklift 150 based on the second detection signal S2. The detection unit 30 controls the indication unit 40a, 40b of the hearing protection device 10 of the first user 100 such that the indication unit 40a, 40b provides an indication to the user 100 if the assigned distance value is at or below a predetermined threshold distance value (not illustrated here, please see FIGS. 11a to 14c for details). FIG. 3 further shows another user 120 wearing a hearing protection device 10' (not visible here), which sends out another detection signal as illustrated by S3. User 120 is working at a machine 170. The detection signal S3 is also received by the receiver 34 of the first user 100. As the distance to the first user 100 is larger compared to the distance between the first and second users 100, 110 (only schematically visible in FIG. 3), the detection unit 30 may not provide an indication to the first user 100 as the assigned distance value is above the predetermined threshold distance value. Similarly, the first detection signal S1 as sent out by the transmitter 32 of the hearing protection device 10 of the first user is received by the receivers of the external device 50 attached to the forklift 150 and of the hearing protection device 10' worn by the third user 120. The detection unit of the external device 50 provides, similarly to the first user, an indication to the second user via the indication unit of the external device 50 as the assigned distance value is at or below a predetermined threshold distance value. As outlined above, this is not given for the third user 120 and thus, the detection unit and the indication unit of the third user 120 do not provide an indication to the third user 120. FIG. 3 shows a static scenario, but the conditions may change as e. g. the forklift 150 is moving and may approach the third user 120 wearing the hearing protection device 10' similar to the above-mentioned scenario for the first user 100. At the same time, the forklift 150 may increase the distance to the first user 100 and thereby the assigned distance value between the first and the second users 100, 110 is above the predetermined threshold distance value, i. e. no indication may be provided to the first user 100 any longer.

FIG. 4 shows in a schematic side view the external device 50 according to an embodiment of the present disclosure. The external device 50, similarly to the hearing protection device 10 as described in FIGS. 1 and 2, comprises a detection unit and an indication unit (both omitted here for simplification). The detection unit also comprises a transmitter sending out a second detection signal S2. The external device 50 further comprises an indication unit (not shown here) providing an indication 42d to a user (not shown) of the external device 50. Furthermore, the external device comprises a receiver (not shown here) for receiving a first detection signal S1 as sent out by a hearing protection device 10 as illustrated in FIG. 3.

FIG. 5 shows in a schematic side view the external device 50 being attached to personal protective equipment 200. As illustrated in FIG. 4 as well, the external device 50 sends out a second detection signal S2 as well as provides an indication 42d to the user of the external device 50 and the personal protective equipment 200, respectively. The personal protective equipment 200 shown in FIG. 5 is a welding shield or welding helmet 200. The external device 50 is attached to the welding helmet 200 by the attachment means 54.

Figure 6:
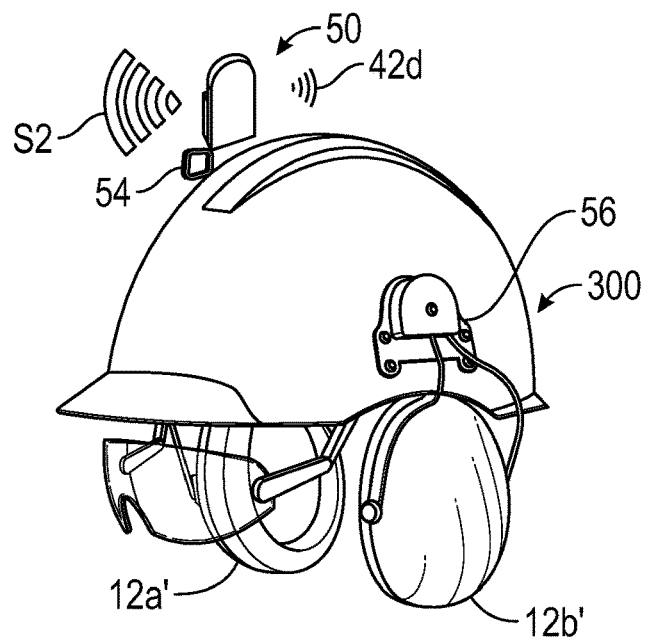
FIG. 6 is a schematic side view of the external device as shown in FIG. 4 being attached to personal protective equipment.

FIG. 6 shows in a schematic side view the external device 50 being attached to personal protective equipment 300. As illustrated in FIG. 4 as well, the external device 50 sends out a second detection signal S2 as well as provides an indication 42d to the user of the external device 50 and the personal protective equipment 200, respectively. The personal protective equipment 300 shown in FIG. 5 is a protective helmet 200. The external device is attached to the protective helmet 300 by the attachment means 54. In addition, FIG. 6 shows attachment means 56 to attach earmuff 12a', 12b' of a hearing protection device 10' to the protective helmet 300.

Figure 7:
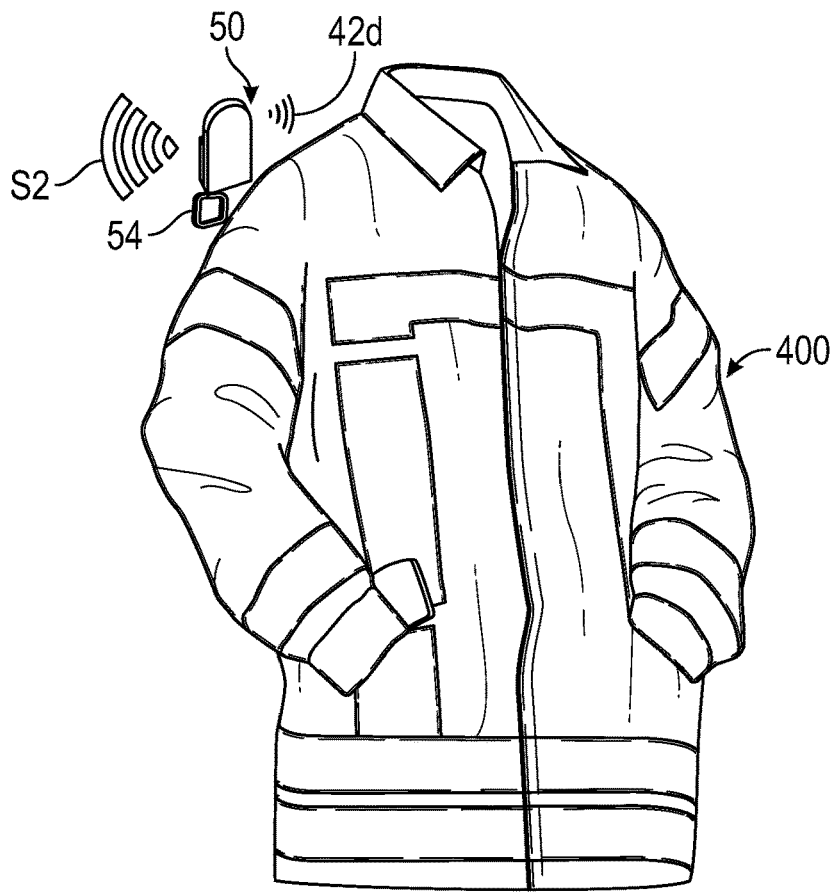
FIG. 7 is a schematic side view of the external device as shown in FIG. 4 being attached to personal protective equipment.

FIG. 7 shows in a schematic side view the external device 50 being attached to personal protective equipment 400. As illustrated in FIG. 4 as well, the external device 50 sends out a second detection signal S2 as well as provides an indication 42d to the user of the external device 50 and the personal protective equipment 400, respectively. The personal protective equipment 400 shown in FIG. 7 is a protective jacket 400. The external device 50 is attached to the protective jacket 400 by the attachment means 54.

Figure 8:
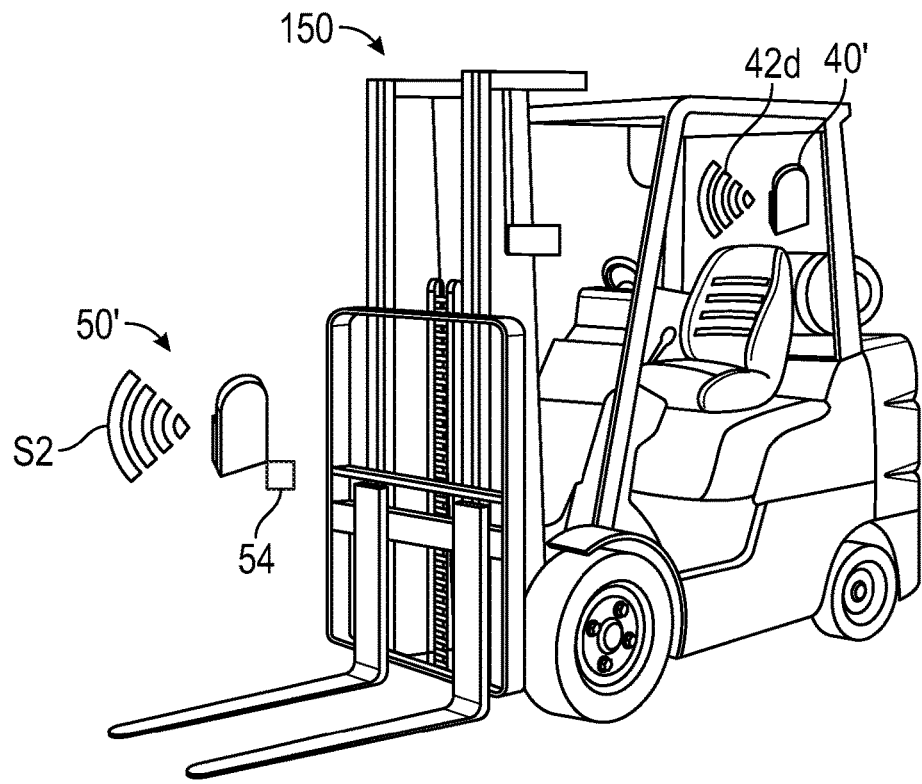
FIG. 8 is a perspective view of a vehicle with an external device according to an embodiment of the present disclosure indicating the second detection signal.

FIG. 8 shows in a schematic side view the external device 50' being attached to a vehicle 150. As illustrated in FIG. 4 as well, the external device 50' sends out a second detection signal S2. The external device 50' further comprises an indication unit 40' providing an indication 42d to a user of the external device 50 and the vehicle 150, respectively. The external device 50' and the indication unit 40' differ from the embodiments as shown in FIGS. 5 to 7 in that the indication unit 40' is in a separate housing spaced from the external device 50'. The indication unit 40' is also attached to the vehicle 150 by an attachment means (not shown here). The vehicle 150 shown in FIG. 8 is a forklift 150. The external device 50' is attached to the forklift 150 by the attachment means 54.

Figure 9:
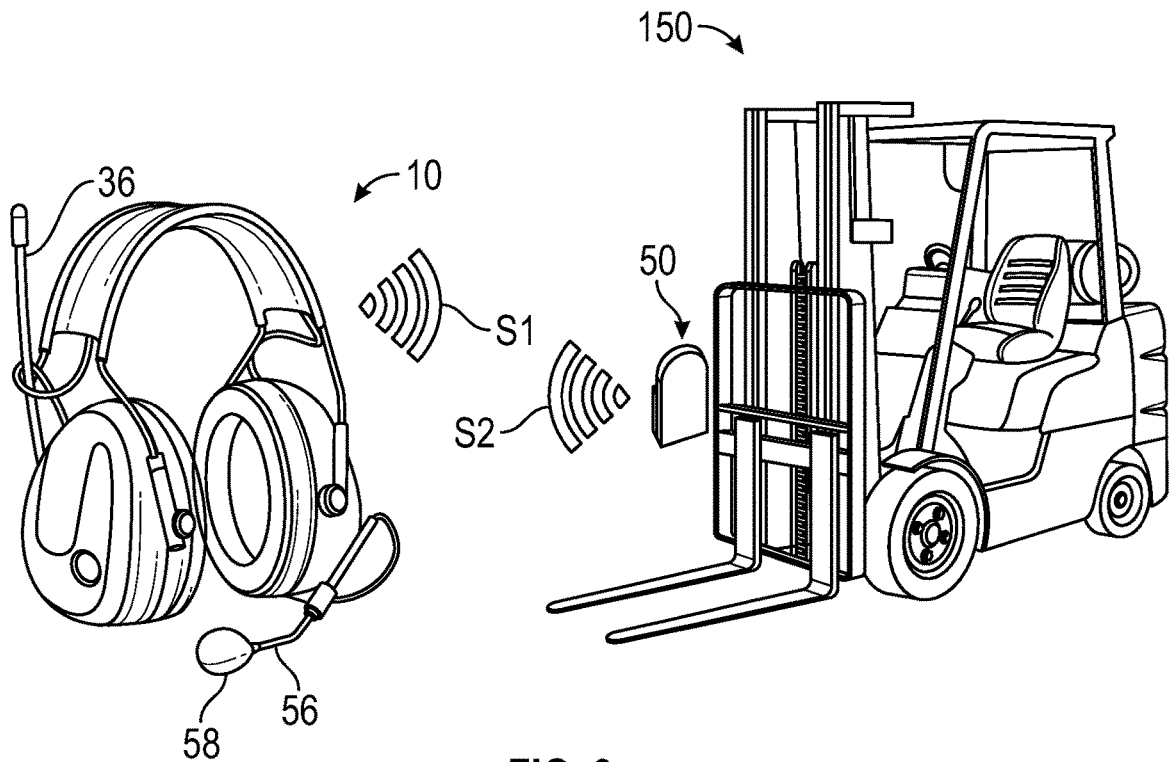
FIG. 9 is a perspective view of a hearing protection device according to an embodiment of the present disclosure indicating a first detection signal and the vehicle as shown in FIG. 8.

FIG. 9 shows in a perspective view a hearing protection device 10 and an external device attached to a vehicle 150, e. g. a forklift 150. As can be seen, the hearing protection device 10 sends via its detection unit 30 and its transmitter 32, respectively, a first detection signal as illustrated by S1. The first detection signal S1 is being received by the receiver of the external device 50 attached to the vehicle 150. In turn, the external device sends out via its detection unit and its transmitter, respectively, a second detection signal as illustrated by S2. The second detection signal S2 in turn is being received by the receiver 34 of the hearing protection device 10. In addition to the embodiment as shown in FIG. 1, the hearing protection device 10 further comprises a microphone 58 mounted to one earmuff of the hearing protection device 10 via the microphone boom 56. Similar to the embodiment as shown in FIG. 2, the hearing protection device comprises an antenna 36, which may help to increase transmission of the first detection signal S1 and/or the receipt of the second detection signal S2.

Figure 10:
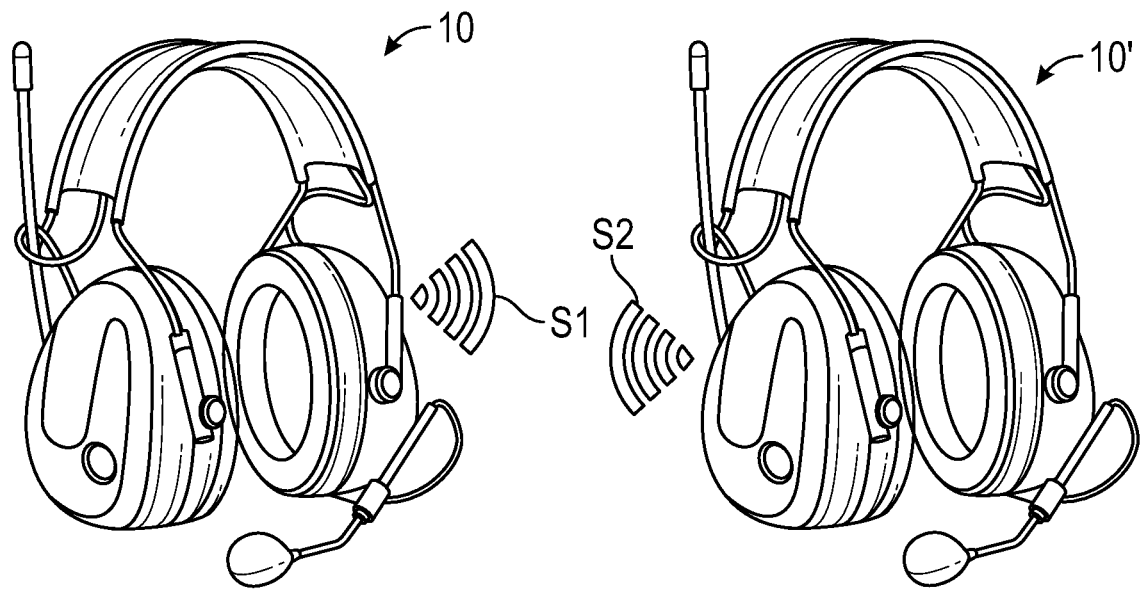
FIG. 10 is a perspective view of a hearing protection device according to an embodiment of the present disclosure indicating a first detection signal and an external device according to the present disclosure being a hearing protection device indicating a second detection signal.

FIG. 10 shows in a perspective view a similar embodiment of the present disclosure as shown in FIG. 9, except that the external device in this case is a second hearing protection device 10'. As can be seen, the first hearing protection device 10 sends via its detection unit 30 and its transmitter 32, respectively, a first detection signal as illustrated by S1. The first detection signal S1 is being received by the receiver of the second hearing protection device 10'.

In turn, the second hearing protection device 10' sends out via its detection unit and its transmitter, respectively, a second detection signal as illustrated by S2. The second detection signal S2 in turn is being received by the receiver 34 of the hearing protection device 10.

Figure 11A:
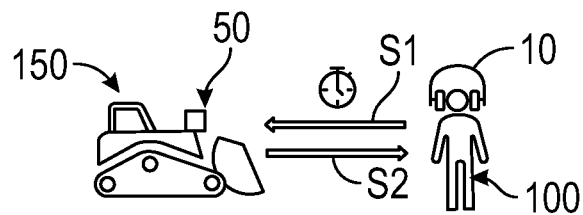
FIG. 11A is a schematic side view of a vehicle with an external device according to an embodiment of the present disclosure indicating the second detection signal and a user with a hearing protection device according to the present disclosure indicating the first and second detection signals.

FIG. 11A is a schematic side view of a vehicle 150 with an external device 50 and a user 100 wearing a hearing protection device 10 according to the present disclosure. As illustrated, the hearing protection device 10 sends out a first detection signal S1 which will be received by the external device 50 of the vehicle 150. In turn, the external device 50 of the vehicle 150 sends out a second detection signal S2 which will be received by the hearing protection device 10 of the user 100. The detection unit 30 of the hearing protection device 10 assigns a distance value representing the physical distance between the user 100 (wearing the hearing protection device 10) and the vehicle 150 (with the attached external device 50) based on the received second detection signal S2. In turn, the detection unit of the external device 50 assigns a distance value representing the physical distance between the user 100 (wearing the hearing protection device 10) and the vehicle 150 (with the attached external device 50) based on the received first detection signal S1. In the embodiment shown, the first and second detection signals S1, S2 are ultra-wide band (UWB) signals and the characteristics of the first and second detection signal S1, S2 for assigning the distance value is based on the time of flight as indicated by the clock icon in FIG. 11A, wherein the time of flight is proportional to the distance. In other words, the longer the time of flight, the larger the distance. It is to be noted, as outlined above, that the predetermined threshold distance value may be different for the different users.

Figure 11B:
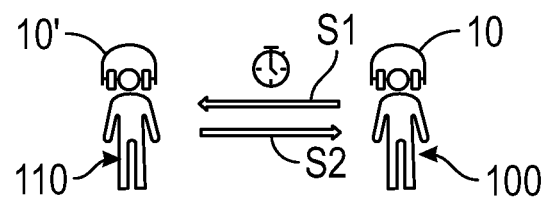
FIG. 11B is a schematic side view of a user with an external device according to an embodiment of the present disclosure being a hearing protection device indicating the second detection signal and a user with a hearing protection device according to the present disclosure indicating the first and second detection signals.

FIG. 11B is a schematic side view of an embodiment of the present disclosure, wherein the external device is a second hearing protection device 10'. FIG. 11B shows a first and a second user 100, 110 each wearing a hearing protection device 10, 10' according to the present disclosure. As illustrated, the first hearing protection device 10 sends out a first detection signal S1 which will be received by the second hearing protection device 10' of the user 110. In turn, the second hearing protection device 10' sends out a second detection signal S2 which will be received by the first hearing protection device 10 of the user 100. The detection unit 30 of the hearing protection device 10 assigns a distance value representing the physical distance between the user 100 (wearing the hearing protection device 10) and the second user 110 (wearing the hearing protection device 10') based on the received second detection signal S2. In turn, the detection unit of the second hearing protection device 10' assigns a distance value representing the physical distance between the user 100 (wearing the hearing protection device 10) and the second user 110 (wearing the hearing protection device 10') based on the received first detection signal S1. In the embodiment shown, the first and second detection signals S1, S2 are ultra-wide band (UWB) signals and the characteristics of the first and second detection signal S1, S2 for assigning the distance value is based on the time of flight as indicated by the clock icon in FIG. 11B, wherein the time of flight is proportional to the distance. In other words, the longer the time of flight, the larger the distance. It is to be noted, as outlined above, that the predetermined threshold distance value may be different for the different users.

Figure 12A:
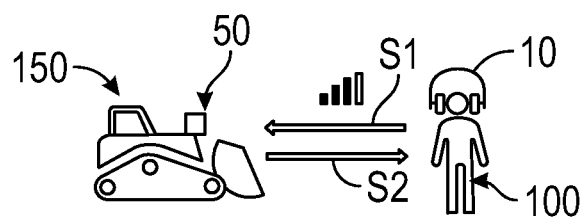
FIG. 12A is a schematic side view of a vehicle with an external device according to an embodiment of the present disclosure indicating the second detection signal and a user with a hearing protection device according to the present disclosure indicating the first and second detection signals.

FIG. 12A shows a similar embodiment as shown in FIG. 11A. FIG. 12A is a schematic side view of a vehicle 150 with an external device 50 and a user 100 wearing a hearing protection device 10 according to the present disclosure. As illustrated, the hearing protection device 10 sends out a first detection signal S1 which will be received by the external device 50 of the vehicle 150. In turn, the external device 50 of the vehicle 150 sends out a second detection signal S2 which will be received by the hearing protection device 10 of the user 100. The detection unit 30 of the hearing protection device 10 assigns a distance value representing the physical distance between the user 100 (wearing the hearing protection device 10) and the vehicle 150 (with the attached external device based on the received second detection signal S2. In turn, the detection unit of the external device 50 assigns a distance value representing the physical distance between the user 100 (wearing the hearing protection device 10) and the vehicle 150 (with the attached external device 50) based on the received first detection signal S1. Different to the embodiment as shown in FIG. 11A, in the embodiment shown here, the first and second detection signals S1, S2 are Bluetooth signals, preferably Bluetooth Low Energy (BTLE) signals and the characteristics of the first and second detection signal S1, S2 for assigning the distance value is based on the signal strength of the received signals as indicated by the signal strength icon in FIG. 12A, wherein the signal strength is proportional to the distance. In other words, the lower the signal strength, the larger the distance. It is to be noted, as outlined above, that the predetermined threshold distance value may be different for the different users.

Figure 12B:
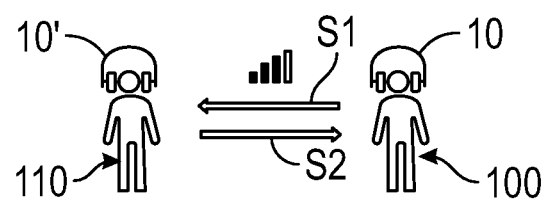
FIG. 12B is a schematic side view of a vehicle with an external device according to an embodiment of the present disclosure being a hearing protection device indicating the second detection signal and a user with a hearing protection device according to the present disclosure indicating the first and second detection signals.

FIG. 12B shows a similar embodiment as shown in FIG. 11B. FIG. 12B is a schematic side view of an embodiment of the present disclosure, wherein the external device is a second hearing protection device 10'. FIG. 11B shows a first and a second user 100, 110 each wearing a hearing protection device 10, 10' according to the present disclosure. As illustrated, the first hearing protection device 10 sends out a first detection signal S1 which will be received by the second hearing protection device 10' of the user 110. In turn, the second hearing protection device 10' sends out a second detection signal S2 which will be received by the first hearing protection device 10 of the user 100. The detection unit 30 of the hearing protection device 10 assigns a distance value representing the physical distance between the user 100 (wearing the hearing protection device 10) and the second user 110 (wearing the hearing protection device 10') based on the received second detection signal S2. In turn, the detection unit of the second hearing protection device 10' assigns a distance value representing the physical distance between the user 100 (wearing the hearing protection device 10) and the second user 110 (wearing the hearing protection device 10') based on the received first detection signal S1. Different to the embodiment as shown in FIG. 11B, in the embodiment shown here the first and second detection signals S1, S2 are ultra-wide band (UWB) signals and the characteristics of the first and second detection signal S1, S2 for assigning the distance value is based on the time of flight as indicated by the signal strength icon in FIG. 12B, wherein the signal strength is proportional to the distance. In other words, the lower the signal strength, the larger the distance. It is to be noted, as outlined above, that the predetermined threshold distance value may be different for the different users.

Figure 13A:
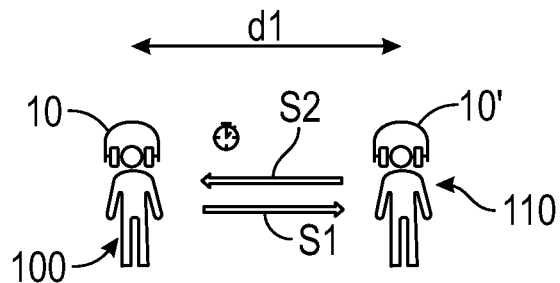
FIG. 13A is a schematic side view of two users with hearing protection devices according to an embodiment of the present disclosure at a certain distance relative to each other.
Figure 13B:
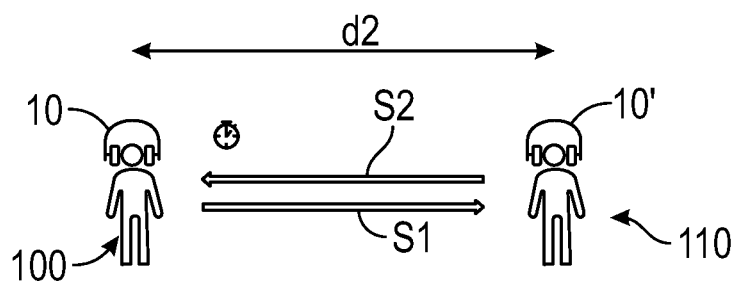
FIG. 13B is a schematic side view of the scenario as shown in FIG. 13A, wherein the distance relative to each other has been increased.
Figure 13C:
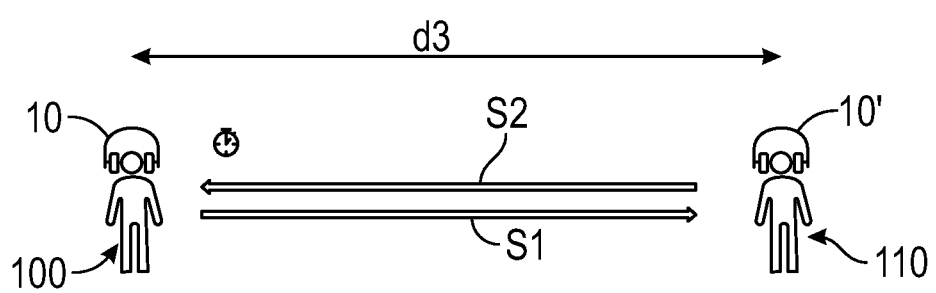
FIG. 13C is a schematic side view of the scenario as shown in FIG. 13A, wherein the distance relative to each other has been further increased.

FIGS. 13A to 13C illustrate in schematic side views two users 100, 110 each wearing a hearing protection device 10, 10' according to the present disclosure, wherein the scenarios shown in each of the Figs. are similar except that the distances d1, d2, d3 between the first and second users 100, 110 are different. FIG. 13A represents the embodiment of FIG. 11B, where the first and second detection signals S1, S2 are UWB signals and where the characteristic of the received signal is the time of flight as illustrated by the clock icon. The two users 100, 110 are spaced apart by the distance d1 leading to a certain time of flight between the two users 100, 110 and their hearing protection devices 10', respectively. In FIG. 13B, a similar set-up is shown, except that the distance d2 between the two users 100, 110 and their hearing protection devices 10, 10', respectively, has been increased relative to distance d1 as indicated in FIG. 13A. This increased distance d2 leads to an increased time of flight between the two users 100, 110 and their hearing protection devices 10, 10', respectively, compared to the time of flight in FIG. 13A. In FIG. 13C, in turn a similar set-up is shown, except that the distance d3 between the two users 100, 110 and their hearing protection devices 10, 10', respectively, has been further increased relative to distance d1 as indicated in FIG. 13A, i. e. the distance d3 as indicated in FIG. 13C is even larger than the already increased distance d2 of FIG. 13B. This further increased distance d3 leads to an increased time of flight between the two users 100, 110 and their hearing protection devices 10, 10', respectively, compared to the time of flight in FIG. 13B.

Figure 14A:
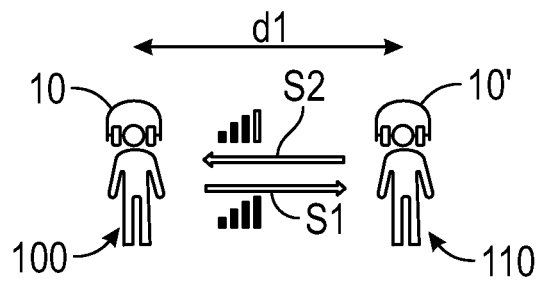
FIG. 14A is a schematic side view of two users with hearing protection devices according to an embodiment of the present disclosure at a certain distance relative to each other.
Figure 14B:
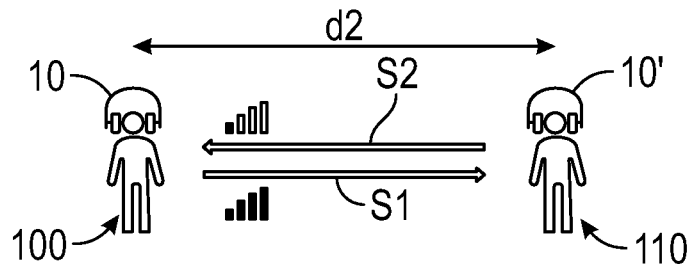
FIG. 14B is a schematic side view of the scenario as shown in FIG. 14A, wherein the distance relative to each other has been increased.
Figure 14C:
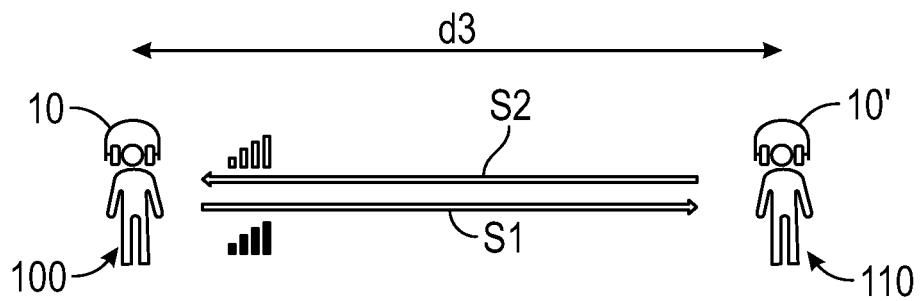
FIG. 14C is a schematic side view of the scenario as shown in FIG. 14A, wherein the distance relative to each other has been further increased.

FIGS. 14A to 14C illustrate in schematic side views two users 100, 110 each wearing a hearing protection device 10, 10' according to the present disclosure, wherein the scenarios shown in each of the Figs. are similar except that the distances d1, d2, d3 between the first and second users 100, 110 are different, similar to as indicated in FIGS. 13A to 13C. FIG. 14A represents the embodiment of FIG. 11B, where the first and second detection signals S1, S2 are Bluetooth signals, preferably Bluetooth Low Energy (BTLE) signals, and where the characteristic of the received signal is the signal strength of the received first and second detection signals S1, S2 as illustrated by the signal strength icon. The two users 100, 110 are spaced apart by the distance d1 leading to a certain signal strength of the received first and second detection signals S1, S2 for the two users 100, 110 and their hearing protection devices 10, 10', respectively, as indicated with the signal strength icon showing 3 of 4 bars for the received signal for the first user 100 and the hearing protection device 10, respectively. In FIG. 14B, a similar set-up is shown, except that the distance d2 between the two users 100, 110 and their hearing protection devices 10', respectively, has been increased relative to distance d1 as indicated in FIG. 13A. This increased distance d2 leads to a lower signal strength of the received first and second detection signals S1, S2 for the two users 100, 110 and their hearing protection devices 10, respectively, compared to the signal strength indicated in FIG. 14A, as indicated by the signal strength icon showing only 1 of 4 bars for the received signal for the first user 100 and the hearing protection device 10, respectively. In FIG. 13C, in turn a similar set-up is shown, except that the distance d3 between the two users 100, 110 and their hearing protection devices 10, 10', respectively, has been further increased relative to distance d1 as indicated in FIG. 14A, i. e. the distance d3 as indicated in FIG. 14C is even larger than the already increased distance d2 of FIG. 14B. This further increased distance d3 leads to an even lower signal strength for the two users 100, 110 and their hearing protection devices 10, 10', respectively, compared to the time of flight in FIG. 14B, as indicated by the signal strength icon showing none of 4 bars for the received signal for the first user 100 and the hearing protection device 10, respectively.

Figure 15:
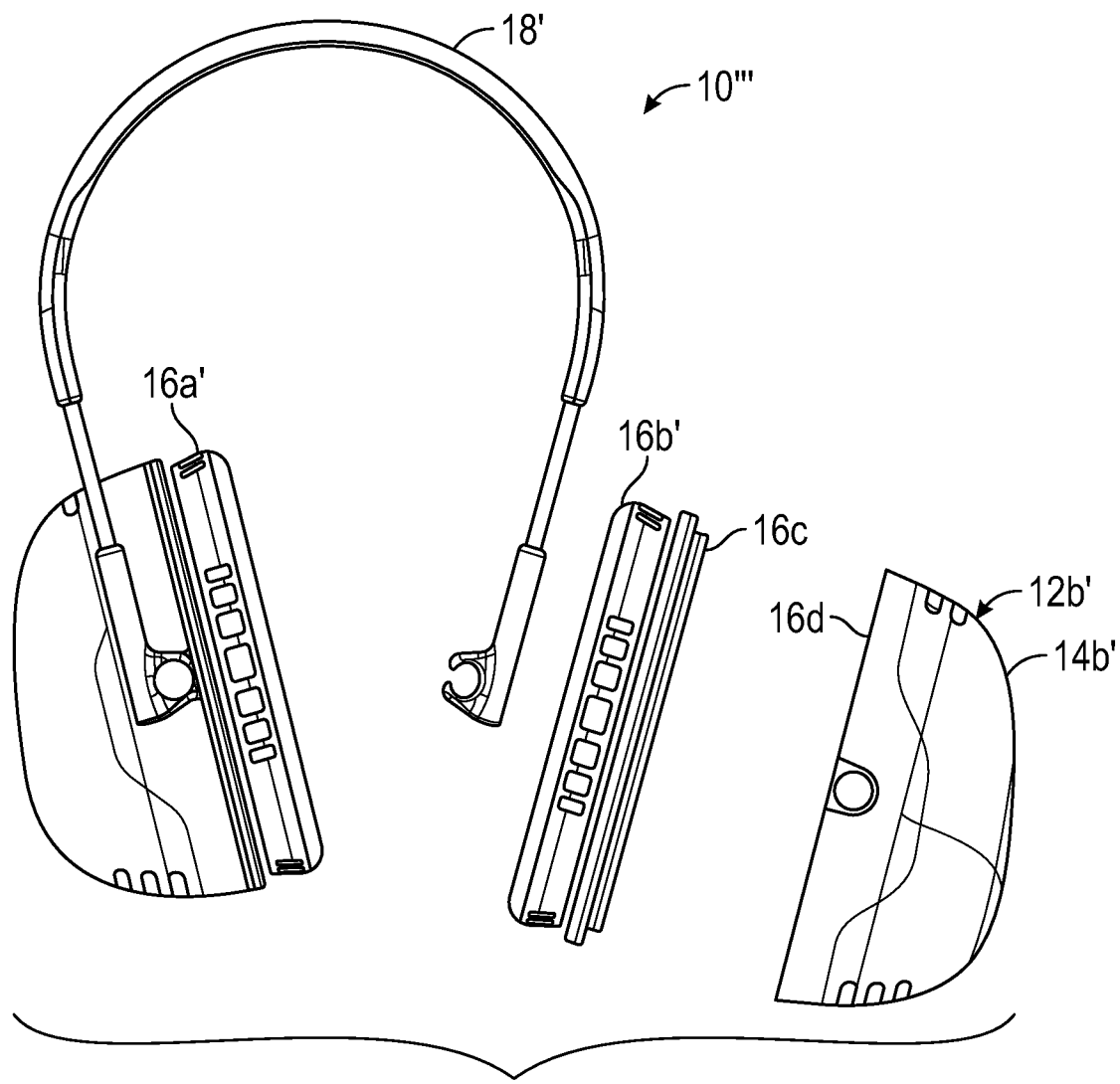
FIG. 15 is a schematic front view of a conventional hearing protection device according to the prior art illustrating the steps of preparation of the method of retrofitting a hearing protection device with a detection unit according to the present disclosure.
Figure 16:
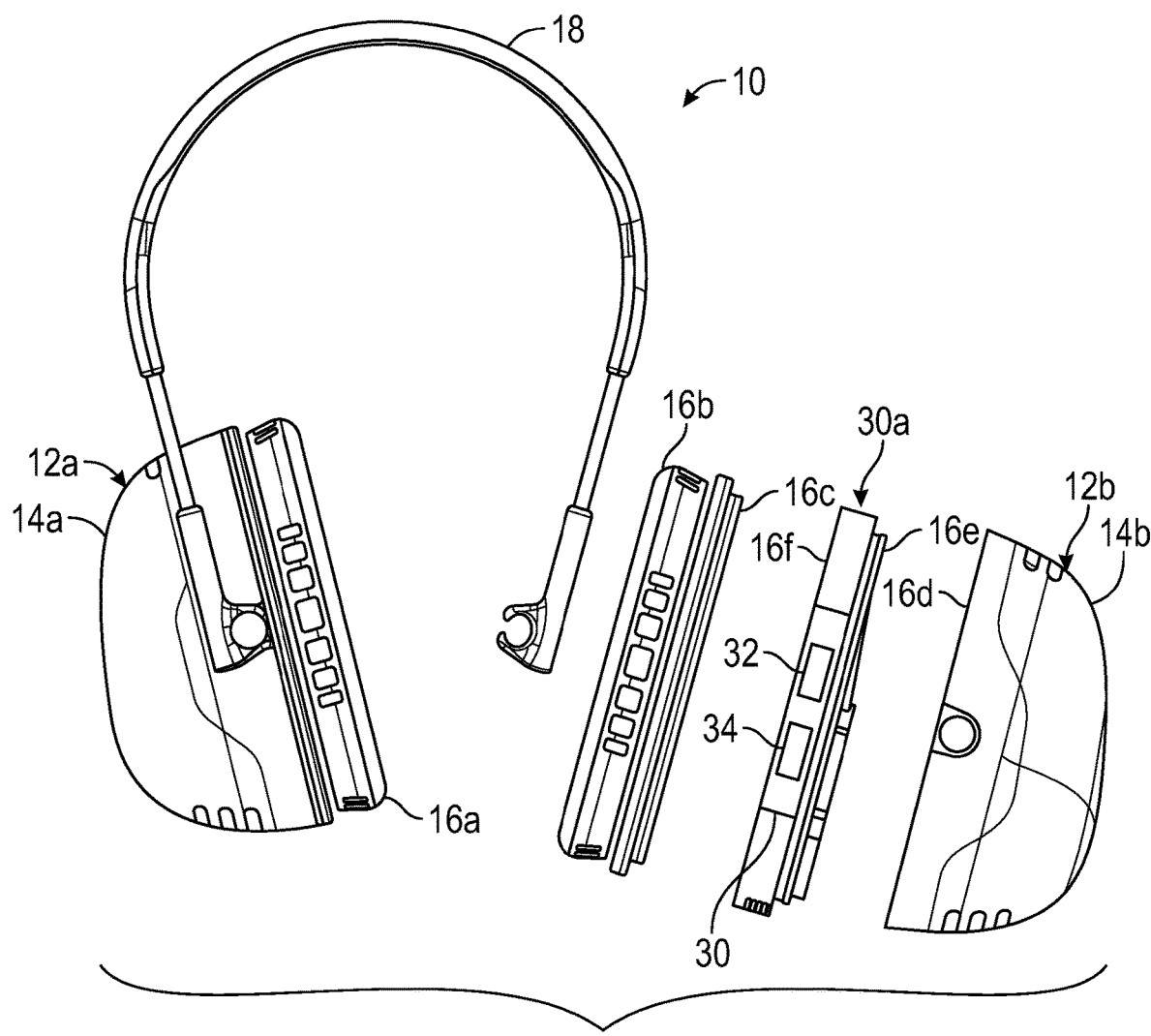
FIG. 16 is a schematic front view of an embodiment of the hearing protection device illustrating the steps of finishing of the method of retrofitting a hearing protection device with a detection unit according to the present disclosure.

FIGS. 15 and 16 each show in a schematic front view an embodiment of the hearing protection device 10, wherein FIG. 15 shows a conventional hearing protection device 10" and wherein FIG. 16 shows the hearing protection device 10 which has been retrofitted with a detection unit according to an embodiment of the present disclosure. FIG. 15 illustrates the method of retrofitting of a conventional hearing protection device 10", wherein the cushion 16b' has been detached from the cup 14b' of earmuff 12b'. In this spaced-apart configuration, the connection means 16c, 16d have been disconnected from each other. In addition, earmuff 12b' has been disconnected from headband 18', although this step may be omitted depending on the dimension, the available space and the skills of the person carrying out the retrofitting method. The other earmuff 12a' is still shown in its original configuration having the cushion 16a' attached to the cup 14a' of the earmuff 12a'. Here, the earmuff 12a' is still connected to the headband 18'. FIG. 16 illustrates the further steps of the method of retrofitting the hearing protection device 10'. The detection unit 30 contained in a mounting ring 30a is placed between the cushion 16a and the cup 14a of the earmuff 12a being in a spaced-apart configuration as provided by the step described above. In a next step, the connection means 16e, 16f of the mounting ring 30a containing the detection unit 30 will be each connected to the connection means 16d of the cup 16b and to the connection means 16c of the cushion 16b. In case that the earmuff 12b had been disconnected from the headband 18, the earmuff 12b needs to be re-connected thereto. The method of retrofitting has been illustrated for one earmuff 12b only for the reason of simplification of FIGS. 15 and 16. It is understood by the skilled person that similar steps are being carried out to complete the method of retrofitting the hearing protection device 10 for the other earmuff 12a as well. However, it is also conceivable that only one earmuff 12b is retrofitted with a detection unit and the other earmuff 12a remains in its original configuration.

Figure 17:
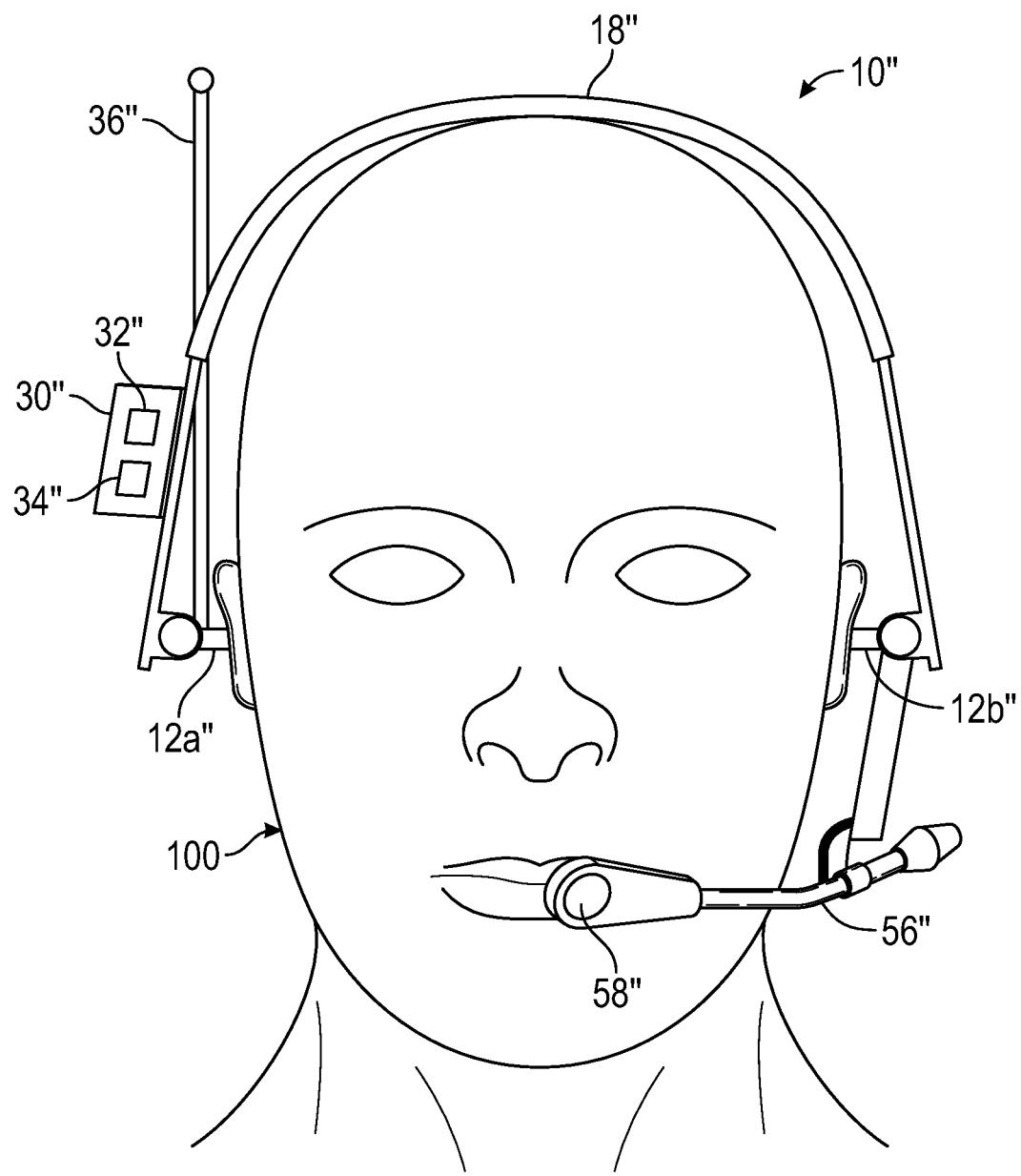
FIG. 17 shows in a schematic front view a hearing protection device according to an embodiment of the present disclosure comprising earplugs.

FIG. 17 shows in a schematic front view a hearing protection device 10" according to another embodiment of the present disclosure. The hearing protection device 10" as shown here is similar to the hearing protection device 10 as illustrated in FIG. 1, except that the hearing protection device 10" comprises earplug 12a", 12b" instead of earmuffs 12a, 12b as illustrated in FIG. 1. In the embodiment shown, the earplugs 12a", 12b" are each connected to a headband 18". The hearing protection device 10" further comprises a detection unit 30" with the transmitter 32" for sending out a first detection signal and a receiver 34" for receiving a second detection signal as sent by an external device 50, 50' or another hearing protection device 10' according to the present disclosure. In addition to the embodiment of FIG. 1, the hearing protection device 10" also comprises an antenna 36" similar to the embodiment as illustrated in FIG. 2. Moreover, the hearing protection device 10" comprises a microphone 58" mounted to the headband 18" by a microphone boom 56". Although not explicitly illustrated in FIG. 17, it is understood by the skilled person, that the earplugs 12a", 12b" comprise loudspeakers (not shown) as part of the indication unit of the hearing protection device 10" for providing an audible indication to the user 100 wearing the hearing protection device 10".

The invention claimed is:

1. A hearing protection device for use in a noisy workplace environment, comprising
 a. two earmuffs or ear plugs configured to attenuate sound from multiple noise sources in the noisy workplace environment,
 b. an indication unit comprising at least one loudspeaker for providing an audible indication to a user wearing the hearing protection device, wherein the two earmuffs or ear plugs comprises the loudspeaker, wherein the loudspeaker is within an attenuated environment of the two earmuffs or earplugs;
c. a detection unit comprising
   i. a transmitter for sending out a first detection signal; and,
   ii. a receiver for receiving, in response to the first detection signal being sent, a second detection signal from an external device, wherein the external device is associated with a movable device that perform mobile transport operations within the noisy workplace environment,
   wherein the detection unit is configured to assign a distance value representing the physical distance to the external device based on the second detection signal;
   wherein the hearing protection device is configured such that the detection unit controls the at least one loudspeaker in the indication unit to audibly alert the user of the hearing protection device if the assigned distance value is at or below a predetermined threshold distance value; and
   wherein the assigned distance value at or below the predetermined threshold distance value indicates that the movable device is approaching the user while the user is engaged in tasks at a workstation or moving within the noisy workplace environment.

2. The hearing protection device according to claim 1, wherein the detection unit is configured to assign the distance value based on a characteristic of the received second detection signal.

3. The hearing protection device according to claim 1, wherein the first and second detection signals are ultra-wide band (UWB) signals and wherein the characteristic of the received second detection signal is the time of flight.

4. The hearing protection device according to claim 1, wherein the first and second detection signals are Bluetooth signals and wherein the characteristic of the received second detection signal is the received signal strength.

5. The hearing protection device according to claim 1, wherein the first and/or second detection signal comprises an ID assigned to the hearing protection device and/or the user thereof.

6. The hearing protection device according to claim 1, wherein the hearing protection device comprises two earmuffs each having a cup and a cushion, the hearing protection device further comprising active and/or passive noise cancellation means.

7. The hearing protection device according to claim 1, wherein the detection unit and the indication unit are contained in a mounting ring attached to the earmuffs between the cup and the cushion.

8. The hearing protection device according to claim 1, wherein the first and/or second detection signal is sent along constant intervals interrupted by constant intervals of no signal sent.

9. The hearing protection device according to claim 1, wherein the first and/or second detection signal is sent along variable intervals interrupted by variable intervals of no signal sent.

10. The hearing protection device of claim 1, wherein the detection unit is configured to operate independently of any base station.

11. The hearing protection device of claim 1, further comprising a user interface operable on the hearing protection device for adjusting the predetermined threshold distance value for collision warnings.

12. The hearing protection device of claim 1, further comprising at least one motion sensor configured to detect a speed of movement by the user, wherein the detection unit is configured to automatically adjust the predetermined threshold distance value based on the detected speed.

13. The hearing protection device of claim 1, further comprising a vibration motor arranged to provide a haptic alert in addition to or instead of the audible indication.

14. A collision warning system for use in a noisy workplace environment comprising
a. a hearing protection device, comprising:
   two earmuffs or ear plugs configured to attenuate sound from multiple noise sources in the noisy workplace environment,
   an indication unit comprising at least one loudspeaker for providing an audible indication to a user wearing the hearing protection device, wherein the two earmuffs or ear plugs comprises the loudspeaker, wherein the loudspeaker is within an attenuated environment of the two earmuffs or earplugs;
   a detection unit comprising
      a transmitter for sending out a first detection signal; and,
      a receiver for receiving, in response to the first detection signal being sent, a second detection signal from an external device,
   wherein the detection unit is configured to assign a distance value representing the physical distance to the external device based on the second detection signal; wherein the hearing protection device is configured such that the detection unit controls the at least one loudspeaker in the indication unit to audibly alert the user of the hearing protection device if the assigned distance value is at or below a predetermined threshold distance value; and wherein the assigned distance value at or below the predetermined threshold distance value indicates that the movable device is approaching the user while the user is engaged in tasks at a workstation within the noisy workplace environment;
b. the external device comprising
   a second detection unit comprising
      a second transmitter for sending out a second detection signal; and,
      a second receiver for receiving the first detection signal sent by the hearing protection device, wherein the external device is associated with the movable device that perform mobile transport operations within the noisy workplace environment.

15. The collision warning system according to claim 14, wherein the external device is a hearing protection device, optionally comprising two earmuffs each having a cup and a cushion and active and/or passive noise cancellation means.

16. The collision warning system according to claim 14, wherein the external device is a self-contained device attachable to a person, a vehicle and/or a personal protective device.

17. A method of retrofitting a hearing protection device for use in a noisy workplace environment with a detection unit, the method comprising:
a) providing a hearing protection device comprising:
   i) two earmuffs or ear plugs configured to attenuate sound from multiple noise sources in the noisy workplace environment, and ii) at least one loudspeaker within an attenuated environment of each earmuff or ear plug;
b) providing a detection unit comprising:
  i) a transmitter for sending out a first detection signal; and
  i) a receiver for receiving, in response to the first detection signal being sent, a second detection signal from an external device, the external device being associated with a movable device that performs mobile transport operations within the noisy workplace environment;
wherein the detection unit is configured to:
  (1) assign a distance value representing the physical distance to the external device based on the second detection signal,
  (2) control the at least one loudspeaker to audibly alert a user wearing the hearing protection device if the assigned distance value is at or below a predetermined threshold distance value, and
  (3) indicate that the assigned distance value at or below the predetermined threshold distance value indicates that the movable device is approaching the user while the user is engaged in tasks at a workstation within the noisy workplace environment; and
c) attaching the detection unit to the hearing protection device.

18. The method according to claim 17 further comprising the step of providing an indication unit for providing an indication to a user (100) of the hearing protection device, wherein the detection unit (30, 30', 30") is configured to control the indication unit (40a, 40b) such that the indication unit (40a, 40b) provides the indication to the user (100) of the hearing protection device (10, 10', 10") if the assigned distance value is at or below the threshold value.

* * * * *